United States Patent [19]

Pack et al.

[11] Patent Number: 4,543,965
[45] Date of Patent: Oct. 1, 1985

[54] METHOD AND DEVICE FOR MEASURING INTRAUTERINE PRESSURE

[75] Inventors: Isak Pack, Beer-Sheva; David Veintraub, Negev; Abraham Yarkoni; Josef Merchuk, both of Beer-Sheva, all of Israel

[73] Assignee: Ben-Gurion University of The Negev Research and Development Authority, Beer-Sheva, Israel

[21] Appl. No.: 502,166

[22] Filed: Jun. 8, 1983

[30] Foreign Application Priority Data

Jun. 13, 1982 [IL] Israel ................................. 66047

[51] Int. Cl.$^4$ ................................. A61B 5/02
[52] U.S. Cl. ................................. 128/748; 128/774
[58] Field of Search ............... 128/748, 738, 774, 775, 128/778; 604/101, 104

[56] References Cited

U.S. PATENT DOCUMENTS

| | | | |
|---|---|---|---|
| 3,610,228 | 10/1971 | Temkin | 127/748 |
| 3,726,273 | 4/1973 | Cole | 128/778 |
| 3,752,150 | 8/1973 | Harris | 128/778 |
| 4,046,139 | 9/1977 | Horn | 128/736 |
| 4,100,923 | 7/1978 | Southern | 604/104 X |
| 4,136,681 | 1/1979 | Hon | 128/748 |
| 4,217,911 | 8/1980 | Layton | 128/748 |
| 4,252,131 | 2/1981 | Hon et al. | 128/748 |
| 4,325,387 | 4/1982 | Helfer | 128/772 X |

FOREIGN PATENT DOCUMENTS 2035453 1/1972 Fed. Rep. of Germany ...... 128/778

Primary Examiner—Edward M. Coven

[57] ABSTRACT

There is provided a device for measuring intrauterine pressure during pregnancy and during labor prior to the rupture of the amniotic membrane. The device comprises an elongated catheter having a uterine end and an instrumentation end, and is introducible with its uterine end into the uterus. The catheter has at least one deformable membrane inflatable by means of a fluid, which membrane is fixedly attached to and, in its noninflated state, substantially closely surrounds, a portion of the catheter substantially contiguous with the uterine end. There is also provided pressure-transmitting means located at said uterine end and at least one conduit, leading from a first end located remote from the uterine end to a second end opening to the outside of the catheter at a point within the membrane-surrounded portion. The first end is fittable with first flow-control means. A method for utilizing this device is also described.

7 Claims, 3 Drawing Figures 4,543,965

METHOD AND DEVICE FOR MEASURING INTRAUTERINE PRESSURE

The present invention relates to a method for measuring intrauterine pressure during late stages of pregnancy and during labor prior to the rupture of the amniotic membrane. The invention furthermore relates to a device for carrying out the method according to the invention.

Fetal monitoring is today a standard procedure during childbirth. Fetal heart rate and intrauterine pressure are usually measured and recorded. The intrauterine pressure is usually measured after the rupture of the amniotic membrane, using a method which provides a catheter that is inserted into the uterine cavity, past the presenting part of the fetus. The pressure changes due to uterine contractions are transmitted from the amniotic fluids to an external pressure-measuring device via a liquid which fills the catheter.

This method cannot be used before the rupture of the amniotic membrane. The only way currently used to evaluate the pressure due to uterine contractions prior to membrane rupture is the method of external monitoring of these contractions, a device for which is described in U.S. Pat. No. 3,913,563. Monitoring is based on the contraction of the muscles in the abdominal wall during labor, and therefore provides only an indirect measure of the internal pressure. What is more, in some cases stiffening of the abdominal wall is due to factors other than uterine contactions and thus no interpretation of uterine contractions can be arrived at by external tocometry.

It is one of the objects of the present invention to overcome the limitations of the prior art methods and to provide a method for measuring intrauterine pressure while the amniotic membranes are still intact.

This the present invention achieves by providing a method for measuring intrauterine pressure during pregnancy and during labor prior to the rupture of the amnionic membrane, comprising the steps of:

providing an elongated catheter having at one end thereof at least one inflatable membrane and pressure-transmitting means for making pressure-transmitting contact with the amniotic membrane, said pressure-transmitting means being connectable to a pressure monitor, said inflatable membrane serving for providing anchorage, inside the uterus, for said catheter and purchase for said pressure-transmitting means;

introducing the end of said catheter via the vagina and the cervical canal into the lower portion of the uterus;

inflating said inflatable membrane with a fluid, until said anchorage and said purchase are established, and monitoring said intrauterine pressure.

The invention further provides a device for measuring intrauterine pressure during pregnancy and during labor prior to the rupture of the amniotic membrane, comprising:

an elongated catheter having a uterine end and an instrumentation end, and being introducible with its uterine end into the uterus;

at least one deformable membrane inflatable by means of a fluid, which membrane is fixedly attached to and, in its noninflated state, substantially closely surrounds, a portion of said catheter substantially contiguous with the uterine end thereof, pressure-transmitting means located at said uterine end;

at least one conduit, leading from a first end located remote from said uterine end to a second end opening to the outside of said catheter at a point within said membrane-surrounded portion, which first end is fittable with first flow-control means.

It will be appreciated that the present invention resides in the provision of the anchoring membrane. While the pressure-monitoring element may be any of the known per se types of pressure transducer and as such part of the monitoring and recording instrumentation, or attached to the instrumentation end of the catheter, or even located at the tip of the catheter, experience has shown that the means transmitting the intrauterine pressure to be monitored to the monitoring or sensing element is advantageously in the form of a relatively small, inflatable membrane located at the tip, and closing off, the uterine end of the catheter. Thus the preferred embodiment of the present invention, discussed and explained in detail hereinafter, makes use of such a membrane.

While the invention will now be described in connection with certain preferred embodiments, it will be understood that it is not intended to limit the invention to these particular embodiments. On the contrary, it is intended to cover all alternatives, modifications and equivalent arrangements as may be included within the scope of the invention as defined by the appended claims. Nevertheless, it is believed that embodiments of the invention will be more fully understood from a consideration of the following illustrative description read in conjunction with the accompanying drawings, in which:

Figure 1:
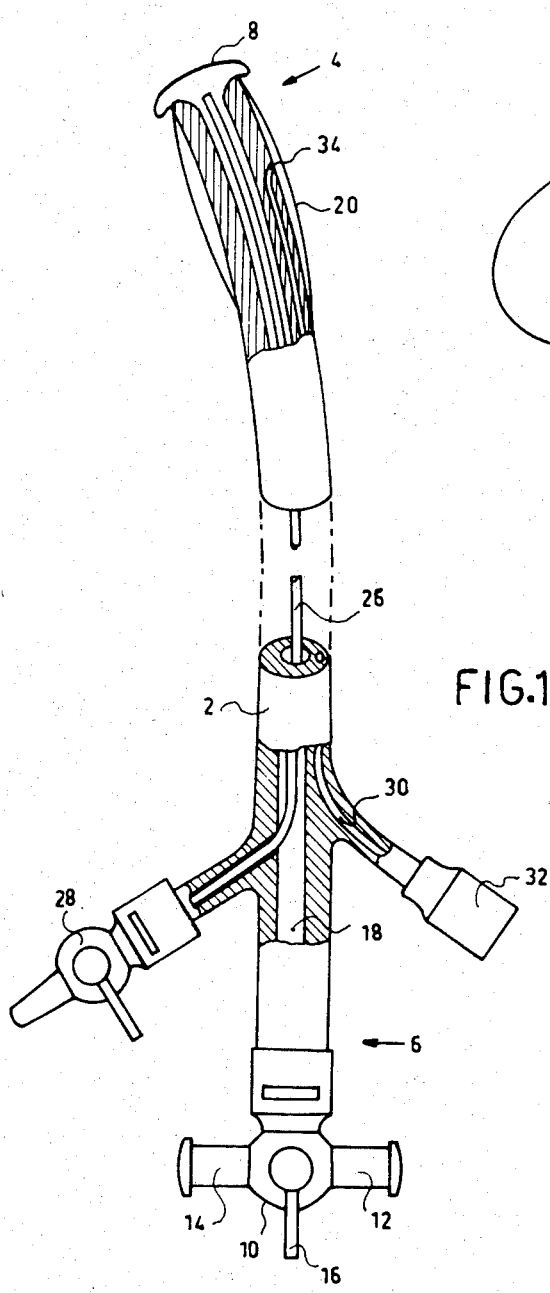
FIG. 1 is a somewhat enlarged view, partly in cross section, of the catheter according to the invention, with the membranes in the deflated state.

There is seen in FIG. 1 an elongated, flexible catheter 2 having a uterine end 4 and an instrumentation end 6. The uterine end 4 is closed by a first, elastically deformable, inflatable membrane 8, shown in FIG. 1 in the limp, collapsed state. The instrumentation end 6 is provided with a three-way stopcock 10 which has two free standard sockets, a first socket 12 attachable to a pressure monitor and recorder which, today, is considered standard equipment for delivery rooms, and a second socket 14, to which, for a purpose to be described further below, a syringe can be attached. By turning the handle 16 of the stopcock 10, the central bore 18 of the catheter 2 can be made to communicate either with the monitor socket 12 or the syringe socket 14. Connection of the catheter to the pressure monitor and recorder is possible by attaching one end of a piece of liquid-filled tubing to the socket 12 and the other end to the monitor. Another, preferable possibility would be the attachment, directly to socket 12, of a pressure transducer, to be connected to the monitor by electric cable. This procedure will minimize the hydraulic system, reduce leakage possibilities and simplify setting of the device.

Figure 2:
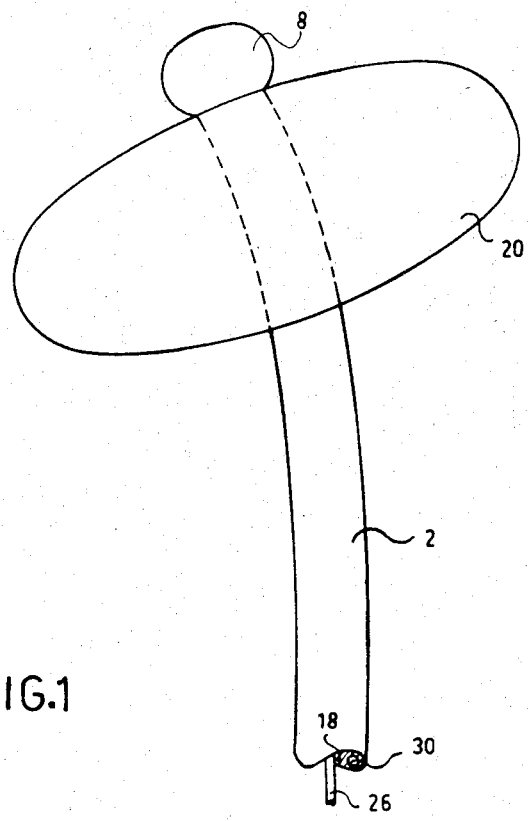
FIG. 2 is a partial view of the catheter and the inflated membranes.
Figure 3:
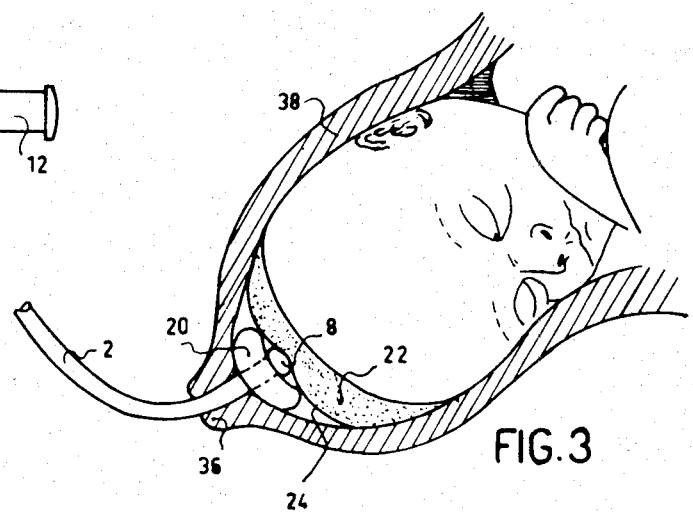
FIG. 3 is a schematic view, in partial cross section, of the catheter in position in the uterus and the two membranes in the inflated state.

Surrounding a portion of the uterine end 4, there is seen another elastically deformable, inflatable membrane 20 which, in the collapsed state shown in FIG. 1, is sleeve-like, with the ends of the sleeve tightly attached to the catheter 2. When inflated (in a manner to be explained in detail further below), this second membrane 20 assumes a toroid shape as shown in FIG. 2, while the first membrane 8 assumes a substantially spherical shape. The purpose of inflating these two membranes has already been indicated in the introductory section of this specification and is also clear from FIG. 3; Intrauterine pressure, transmitted by the amniotic fluid 22 to the amniotic membrane 24, is sensed by the inflated membrane 8 which transmits this pressure via the bore 18 of the catheter 2 to the pressure monitor and recorder, to which the catheter 2 is connected via the socket 12. The inflated membrane 20, on the other hand, provides an anchorage for the catheter 2 and a point of purchase for the inflated, pressure-transmitting membrane 8.

The fluid used for inflating the membranes 8 and 20 is a sterile liquid (e.g., distilled water). In order not to excessively dampen the contraction-caused pressure fluctuations on their way from the membrane 8 via the catheter 2 to the pressure monitor, the liquid column extending from the outermost point of the pressure-transmitting membrane 8 to the pressure monitor must not contain air bubbles or pockets. This problem is taken care of by a special bleeding procedure for which there is provided a conduit in the shape of a thin tube 26 (FIG. 1), one end of which is located outside of the catheter 2 at a point close to the instrumentation end 6 of the latter, and the other end of which is located inside the catheter 2, almost reaching its end 4. The outside end of the tube 26 is connected to a simple stopcock 28. The bleeding procedure is part of the inflation procedure for the pressure-transmitting membrane, and is carried out as follows: A syringe (not shown) is connected to the socket 14 of the stopcock 10, and the handle 16 is turned to the position in which the syringe is connected with the bore 18 of the catheter 2. The stopcock 28 is opened and liquid from the syringe is injected into the catheter 2. The air present in the bore 18 is pushed towards the uterine end 4, whence it can escape, mixed with some liquid, through the thin tube 26 and the stopcock 28. When the escaping liquid jet becomes smooth and continuous, it can be taken as a sign that all air has been removed, at which point the stopcock 28 is closed.

Inflating the anchoring membrane 20 is carried out via a second conduit 30 which leads from a one-way valve 32 outside of the catheter and close to its instrumentation end 6, to a point 34 within the catheter portion surrounded by the (in the collapsed state) sleeve-like membrane 20, at which point 34 the conduit 30 opens to the outside of the catheter 2. As can be seen from FIG. 1, the conduit 30 is for most of its way embedded in, or part of, the wall of the catheter 2.

The one-way valve 32, as such known, is of the rubberflap type that will permit a liquid to pass when introduced at a certain pressure, e.g., by a syringe, but will not permit the liquid to return, even under higher pressure. Forcing a liquid into the valve 32 will thus inflate the anchoring membrane 20.

In the above, the components of the device have been explained in detail, as have been the inflation procedures, although not necessarily in proper sequence for actual use of the device according to the invention. This sequence is now given below.

The catheter 2, with membranes 8 and 20 collapsed, is introduced via the vagina and the cervix 36 (FIG. 3) into the lower portion of the uterus 38. First to be inflated, using the above-described procedure, is the anchoring membrane 20. The catheter 2 is then attached to the pressure monitor and the above-described bleeding and inflation procedure for the pressure-transmitting membrane 8 initiated. Included in this stage is also the as such known (and therefore not described) calibration procedure. It should be added here that, in most cases, the membrane 8 will not be fully inflated after bleeding is completed, as, with the stopcock 28 open, pressure in the catheter 2 is too low for full inflation. After closing the stopcock 28, it is therefore necessary to add more liquid from the syringe. The stopcock 10 is then turned to the position where the catheter 2 communicates with the monitor, and recording can begin.

It should be noted here that in most cases the catheter is quite easily introduced into the cervical canal. Whenever technical difficulties are encountered, a vaginal speculum or a guide tube can be resorted to.

Withdrawal of the device is very simple: the catheter 2 having been disconnected from the monitor, the pressure-transmitting membrane 8 will collapse. (Alternatively it is also possible to open the stopcock 28). The anchoring membrane 20 is collapsed by inserting a small piece of tubing (e.g., a hypodermic needle) into the one-way valve 32, which is thereby kept open. The liquid inside the inflated anchoring membrane 20 will thus be expelled by the elastic force of the membane 20 tending to return to its original sleeve-like shape and assisted by the pressure exerted by the uterine membrane. The two membranes 8 and 20 having collapsed, the device is now easily withdrawn from the uterus.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for measuring intrauterine pressure during pregnancy and during labor prior to the rupture of the amnionic membrane, comprising the steps of:
   providing an elongated catheter having at one end thereof at least one first inflatable membrane and pressure-transmitting means in the form of a second inflatable membrane for making pressure-transmitting contact with the amniotic membrane, said second inflatable membrane being connectable to a pressure monitor, said first inflatable membrane serving for providing anchorage, inside the uterus, for said catheter and purchase for said second inflatable membrane;
   introducing the end of said catheter via the vagina and the cervical canal into the lower portion of the uterus;
   inflating said first inflatable membrane with a fluid, until said anchorage and said purchase are established;

inflating said second membrane with fluid, and establishing communication between said second membrane and said pressure monitor, and monitoring said intrauterine pressure.

2. The method as claimed in claim 1, further comprising the step of bleeding all air from said catheter while inflating said second membrane.

3. A device for measuring intrauterine pressure during pregnancy and during labor prior to the rupture of the amniotic membrane, comprising:

an elongated catheter having a uterine end and an instrumentation end, and being introducible with its uterine end into the uterus;

at least one first deformable membrane inflatable by means of a fluid, which membrane is fixedly attached to and, in its noninflated state, substantially closely surrounds, a portion of said catheter substantially contiguous with the uterine end thereof, and in its inflated state assumes a substantially toroid shape providing an anchorage for the catheter in the uterus;

a second deformable membrane inflatable by means of a fluid and constituting pressure-transmitting means, said second membane being located at said uterine end and disposed externally of said first membrane; and at least one conduit, leading from a first end located remote from said uterine end to a second end opening to the outside of said catheter at a point within said first membrane-surrounded portion, which first end is fittable with first flow-control means.

4. The device as claimed in claim 3, further comprising second flow-control means, fittable to said instrumentation end, said second flow-control means being adapted to selectively connect said instrumentation end alternatively to instrumentation for the monitoring and/or recording of said intrauterine pressure, and to syringe means for inflating said additional membrane;

an additional conduit for the bleeding of air from said catheter and said additional membrane during the inflation thereof, said additional conduit leading from a first end thereof located outside said catheter close to the instrumentation end thereof, to a second end located inside said catheter close to the uterine end thereof, which first end is fittable with third flow-control means to close off said additional conduit after said bleeding of air.

5. The device as claimed in claim 3, wherein said first flow-control means is a one-way valve.

6. The device as claimed in claim 3, wherein said second flow-control means is a three-way stopcock.

7. The device as claimed in claim 3, wherein said third flow-control means is a two-way stopcock.

* * * * *